United States Patent [19]

Guerrant et al.

[11] Patent Number: 4,820,714

[45] Date of Patent: Apr. 11, 1989

[54] **USE OF PHOSPHOLIPASE INHIBITORS IN THE TREATMENT OF *CLOSTRIDIUM DIFFICILE* DIARRHEA**

[75] Inventors: Richard L. Guerrant, Charlottesville; Aldo M. Lima, University Garden, both of Va.

[73] Assignee: University of Virginia Alumni Patents Foundation, Charlottesville, Va.

[21] Appl. No.: 858,674

[22] Filed: May 2, 1986

[51] Int. Cl.$^4$ .................... A61K 31/44; A61K 31/225
[52] U.S. Cl. ................................ 514/297; 514/547; 514/867
[58] Field of Search .................. 514/297, 547, 867; 424/10

[56] References Cited

U.S. PATENT DOCUMENTS 4,239,780 12/1980 Wallach .............................. 514/647

OTHER PUBLICATIONS

Emeis J. J.; Kluft C., Blood, 1985, 66/1, (86-91).
Rao G. H. R.; White J. G., Agents Actions, 1985, 16/5, (425-434).
Parente L.; Flower R. J., Life Sci., 1985, 36/13, (1225-1231).
Peters S. P. et al., Respiration, 1986, 50/Suppl. 2, (116-122).
Maridonneau—Parini I.; Tauber A. I., Biochem. Biophys. Res. Comm., 1986, 138/3, (1099-1105).
Metz S. A., Diabetes, 1986, 35/7, (808-817).

*Primary Examiner*—Frederick E. Waddell
*Attorney, Agent, or Firm*—John J. Byrne; Bradford E. Kile

[57] ABSTRACT

Hemorrhagic fluid secretion and histologic damage to the intestinal mucosa by *C. difficile* toxin is blocked by the use of phospholipase inhibitors.

12 Claims, No Drawings

USE OF PHOSPHOLIPASE INHIBITORS IN THE TREATMENT OF CLOSTRIDIUM DIFFICILE DIARRHEA

BACKGROUND OF THE INVENTION

The bacterial-mediated diarrheal diseases include cholera, typhoid fever, traveller's diarrhea, and diarrheal illness in infants. The diseases are basically of two types, invasive and non-invasive gastroenteritis. Typhoid fever is representative of the invasive type of disease, which is characterized by invasion of the intestinal mucosa by the pathogen. In the non-invasive type of gastroenteritis, the symptoms are effected by bacterial toxins which stimulate an enormous increase in the secretory activity of the cells lining the small intestine causing an acute loss of body fluid. Although mild diarrhea is a common side effect of antibiotics, sometimes the diarrhea is severe or protracted andthe patient is found to have colitis, often with nodular pseudomembraneous plaques.

A major recognized cause of antibiotic-associated diarrhea and pseudomembraneous colitis is *Clostridium difficile* which produces toxins that cause intestinal cell damage and fluid secretion. (Bartlett *Rev. Infect. Dis.* 1,539 (1979)). Two toxins produced by pathogenic *C. difficile* have been identified from patients with antibiotic-associated colitis. Toxin A causes hemorrhagic fluid secretion and intestinal damage. Libby et al. *Infec. Immun.* 35, 374 (1982). Toxin B is a potent cause of cell damage in tissue culture cells. Both toxins appear to play separate immunological roles in causing antibiotic-assiciated diarrhea and pseudomembraneous colitis.

The detection of an identifiable microbial pathogen provided a rationale for prior forms of therapy. Prior therapy includes antibiotics directed against *Clostridium difficile*, or anion exchange resins that bind the toxin of *Clostridium difficile*. An example of antibiotic which has been directed against *Clostridium difficile* is vancomycin. (Fekdety, *Microbiology*, 1979, 276–279). Diarrhea, fever and toxicity were reported as markedly reduced 2 to 3 days after beginning vancomycin therapy. Oral cholestyramine, an anion-binding resin that may bind the toxin in the colon, has also been used to treat *C. difficile* diarrhea. (Fekety, supra).

A need exists for a direct, antitoxic treatment for *Clostridium difficile* pseudomembraneous colitis and antibiotic-associated diarrhea.

SUMMARY OF THE INVENTION

It has now been found that the use of phospholipase inhibitors provides a direct, antitoxic treatment for *Clostridium difficile* pseudomembraneous colitis and antibiotic-associated diarrhea. Both hemorrhagic fluid secretion and histologic damage to the intestinal mucosa are blocked by the use of phospholipase inhibitors.

DETAILED DESCRIPTION OF THE INVENTION

The invention provides a direct, antitoxic treatment for *Clostridium difficile* pseudomembraneous colitis and antibiotic-associated diarrhea. Prior investigators have studied Clostridium toxin in vitro from stool samples from patients with pseudomembraneouos colitis. See, e.g. Kappas, et at. *British Medical Journal*, 1, 675–678 (1978). However, the present invention is based on the use of an in vivo rabbit ileal ligated loop model. It has been found that the secretory and intestinal damaging effects of *Clostridium difficile* toxin A are reproduced in this rabbit ileal ligated loop model with the same time course and dose responses. (Lima et al., *Clin. Research* 34, 442A (1986)). Surprisingly, it has been found that substances which do not alter the in vitro effects of toxin A may be shown using the rabbit ileal ligated loop model to completely block the damaging effects of toxin A.

The rabbit ileal ligated loop model has been described by Evans et al., *Infect. Immun.*, 7, 873–880 (1973). The present invention involves the use of ligated ileal segments from 4 to about 6 cm long using double ties with umbilical tape between ligated segments, in New Zealand White Rabbits weighing about 1.5 to 2.5 kg under ketamine anesthesia. Using this rabbit ileal ligated loop model, the effects of highly purified, partially purified and crude toxin A preparations have been studied using 3 to 10 µg/ml purified toxin A per loop. As mentioned above, toxin A causes hemorrhagic fluid secretion and intestinal damage. Fluid secretion in the model was determined by examining the volume of fluid secreted per unit length in ml/cm. The histology of the intestinal mucosa was examined after 5 to 6 hours. As shown in Table 1 below, toxin A consistently causes voluminous hemorrhagic secretion.

TABLE 1

| | Effect of Toxin A | |
|---|---|---|
| | C. difficile Toxin A (10 µg) | Buffer Control |
| Mean V/L (ml/cm) | 1.37 | 0.03 |
| ±SD | ±0.39 | ±0.04 |
| Range | 0.76–1.75 | 0–0.13 |
| n | 7 | 7 |

Surprisingly, it has been found that phospholipase inhibitors provide a direct, antitoxic treatment for *Clostridium difficile* pseudomembraneous colitis and antibiotic-associated diarrhea. Suitable phospholipase inhibitors include quinacrine, and Rosenthal's Inhibitor. Quinacrine, also known as Atabrine ®-brand quinacrine by Winthrop-Breon Laboratories, is a 9-alkylamino acridine. It was developed as a potential antimalarial drug by Mietzsch and Mauss, and is described in German Pats. Nos. 553,072 and 571,499 (1934) and U.S. Pat. No. 2,113,357 (1938). The pharmacology of quinacrine was reviewed by Wolfe in *Antibiotics*, 3, 203–233, J. W. Corcoran and F. E. Hahn Eds. (Springer-Verlag 1975). Wolfe identifies quinacrine as d,1-9-(4-diethylamino-1-methylbutylamino)-7-methoxy-3-chloroacridene, a planar heterocyclic compound having a molecular weight of 400 daltons.

Rosenthal's Inhibitor is another example of a phospholipase inhibitor useful in the practice of the present invention. The preparation of Rosenthal's Inhibitor was described by Rosenthal in the *Journal of Biological Chemistry*, 253, 2202–2206 (1960). Rosenthal's Inhibitor is dimethyl d,1-2,3-distearoyloxypropyl-2'-hydroxyethyl ammonium acetate.

Surprisingly, $10^{-5}$ M phospholipase inhibitor eliminated hemorrhagic secretions caused by *Clostridium difficile* toxin A. As illustrated in Table 2 below, quinacrine 4.7 µg/ml, $10^{-5}$ M, completely inhibited fluid secretion caused by toxin A. The inhibition of toxin A effects in adjacent ligated loops suggests that the phospholipase inhibitor is active both in the intestine and is absorbed sufficiently to act in other loops via circulation to block the fluid secretion caused by the toxin. Additional experiments with another phospholipase inhibitor, Rosenthal's inhibitor ($10^{-5}$ M), also shows that it blocks toxin-induced secretion both in the loop with the toxin, and in two adjcent loops. These results confirm that the quinacrine and Rosenthal Inhibitor both act by inhibition of phospholipase, an absorbed pharmacologic effect rather than a direct action of the drug on the toxin.

TABLE 2

Inhibition of C. difficile-induced secretion by Quinacrine

|  | Toxin A* and Quinacrine ($10^{-5}$M) | Toxin A* (Quinacrine in adjacent loops) |
| --- | --- | --- |
| Mean V/L (ml/cm) | 0.05 | 0.08 |
| ±SD | ±0.03 | ±0.07 |
| Range | 0.02–0.07 | 0.02–0.14 |
| n | 4 | 4 |

*Three toxin A lots, purified (10 μg/ml), partially purified, and crude were tested with 1 ml of $10^{-5}$M quinacrine.

In the practice of the present invention, the phospholipase inhibitors used in the treatment of *Clostridium difficile* may be administered orally or parenterally. It has been found that quinacrine is effective to suppress hemorrhagic fluid secretion and histologic damage to intestinul mucosa in solutions of about 5 μm/ml, $10^{-5}$ M. Atabrine ®-brand quinacrine by Winthrop-Breon Laboratories is supplied as tablets of 100 mg, which may be used in the practice of the invention.

It is understood that various other modifications will be apprent to and can readily be made by those skilled in the art without departing from the scope and spirit of this invention. Accordingly, it is not intended that the scope of the claims appended hereto be limited to the description as set forth above, but rather that the claims be construed as encompassing all of the features of patentable novelty which reside in the present in the invention, including all features which would be treated as equivalents thereof by those skilled in the art to which this invention pertains.

What is claimed is:

1. A method of treating antibiotic-associated diarrhea in animals and humans, comprising administering an effective amount to reduce hemorrhagic fluid secretion of a composition of a phospholipase inhibitor selected from the group consisting of quinacrine, quinacrine hydrochloride and dimethyl d,1-2,3-distearoyloxypropyl-2'-hydroxyethyl ammonium acetate and pharmaceutically acceptable acid addition salts, and a pharmaceutical therefor.

2. The method set forth in claim 1, wherein said phospholipase inhibitor is quinacrine hydrochloride.

3. The method set forth in claim 2, wherein said composition is a tablet.

4. The method set forth in claim 1, wherein said phospholipase inhibitor is dimethyl d,1-2, 3-distearoyloxypropyl-2'-hydroxyethyl ammonium acetate.

5. A method of treating pseudomembraneous colitis in animals and humans comprising administering an effective amount to reduce inflammation of the colon of a composition of a phospholipase inhibitor selected from the group consisting of quinacrine, quinacrine hydrochloride and and dimethyl d,1-2,3-distearoyloxypropyl-2'-hydroxyethyl ammonium acetate and pharmaceutically acceptable acid addition salts, and a pharmaceutical vehicle therefor.

6. The method set forth in claim 5, wherein said phospholipase inhibitor is quinacrine hydrochloride.

7. The method set forth in claim 6, wherein said composition is a tablet.

8. The method set forth in claim 5, wherein said phospholipase inhibitor is dimethyl d,1-2, 3-distearoyloxypropyl-2'-hydroxyethyl ammonium acetate.

9. A method of treating *Clostridium difficile* toxins in animals and humans comprising administering an effective amount to reduce hemorrhagic fluid secretion of a composition of a phospholipase inhibitor selected from the group consisting of quinacrine, quinacrine hydrochloride and dimethyl d, 1-2,3-distearoyloxypropyl-2'-hydroxyethyl ammonium acetate and pharmaceutically acceptable acid addition salts, and a pharmaceutical vehicle therefor.

10. The method set forth in claim 9, wherein said phospholipase inhibitor is quinacrine hydrochloride.

11. The method set forth in claim 9, wherein said composition is a tablet.

12. The method set forth in claim 9, wherein said phospholipase inhibitor is dimethyl d, 1-2,3-distearoyloxypropyl-2'-hydroxyethyl ammonium acetate.

* * * * *